(12) United States Patent
Bake et al.

(10) Patent No.: US 8,545,638 B2
(45) Date of Patent: Oct. 1, 2013

(54) METHOD OF CLEANING A FOOD PLANT

(75) Inventors: Klaus Bake, Glinde (DE); Roland Ringstrom, Veberod (SE)

(73) Assignee: Tetra Laval Holdings & Finance SA, Pully (CH)

( * ) Notice: Subject to any disclaimer, the term of this patent is extended or adjusted under 35 U.S.C. 154(b) by 1010 days.

(21) Appl. No.: 11/578,943

(22) PCT Filed: Apr. 21, 2005

(86) PCT No.: PCT/SE2005/000590
§ 371 (c)(1),
(2), (4) Date: Aug. 2, 2007

(87) PCT Pub. No.: WO2005/102546
PCT Pub. Date: Nov. 3, 2005

(65) Prior Publication Data
US 2008/0276968 A1  Nov. 13, 2008

(30) Foreign Application Priority Data

Apr. 22, 2004 (SE) ...................................... 0401030

(51) Int. Cl.
*B08B 9/032* (2006.01)
(52) U.S. Cl.
USPC .................. 134/22.12; 134/22.13; 134/22.17; 134/22.18; 134/28; 134/29
(58) Field of Classification Search
None
See application file for complete search history.

(56) References Cited

U.S. PATENT DOCUMENTS

| | | | | |
|---|---|---|---|---|
| 3,762,874 A | * | 10/1973 | Berry | 422/28 |
| 4,015,618 A | | 4/1977 | Schmid | |
| 4,056,921 A | * | 11/1977 | Gilliand et al. | 53/167 |
| 4,212,761 A | * | 7/1980 | Ciaccio | 510/234 |
| 5,405,452 A | * | 4/1995 | Anderson et al. | 134/22.12 |
| 2005/0183744 A1 | * | 8/2005 | Staub et al. | 134/22.1 |

FOREIGN PATENT DOCUMENTS

| | | |
|---|---|---|
| DE | 21 06 223 | 8/1972 |
| EP | 1 177 841 B1 | 2/2002 |
| JP | 2004-66159 | 3/2004 |

OTHER PUBLICATIONS

Computer translation of WO 00/67561 by Schwarz, published Nov. 16, 2000.*

* cited by examiner

*Primary Examiner* — Michael Kornakov
*Assistant Examiner* — Ryan Coleman
(74) *Attorney, Agent, or Firm* — Buchanan Ingersoll & Rooney PC

(57) ABSTRACT

A method of cleaning a food plant of the type which produces an aseptic product or a product with extended shelf life involves at least one circulation with an alkaline detergent solution and at least one circulation with an acidic cleaning solutions. The circulations take place alternatively with the alkaline detergent solution and the acidic cleaning solution. Prior to the first circulation, between each circulation and after the last circulation, rinsings with water take place. Simultaneously with the last circulation with alkaline detergent solution the plant is sterilized, and after the last circulation with the acidic cleaning solution the two last rinsings with water take place with sterile liquid.

9 Claims, 1 Drawing Sheet

METHOD OF CLEANING A FOOD PLANT

TECHNICAL FIELD

Figure 1:
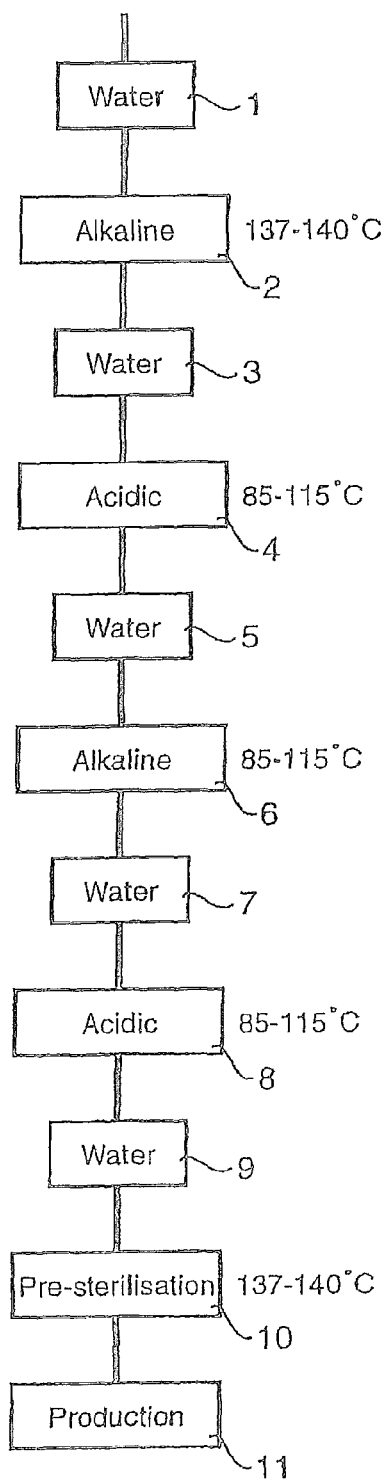

The present invention relates to a method of cleaning a food plant of the type which produces an aseptic product or a product of extended shelf life, the method comprising circulations alternatingly with an alkaline detergent solution and an acidic detergent solution, with interspersed rinsing with water, the circulations including at least one circulation with the alkaline detergent solution and at least one circulation with the acidic detergent solution.

BACKGROUND ART

Within all food production, not least in the dairy industry, a meticulous cleaning of all production equipment is an imperative requirement for good production. Careless hygiene may involve serious consequences, since milk is a perfect nutrient bed where bacteria rapidly multiply. When foods are produced, such as milk products that are aseptic, i.e. they can be stored without refrigeration, all parts of the plant must moreover be sterilised after cleaning and before production begins. This also applies to so-called ESL products (Extended Shelf Life), i.e. products with extended shelf life that are kept in cold storage.

Today, most dairy equipment is cleaned using automatic cleaning CIP (Cleaning In Place). In this instance, the cleaning takes place in circulation cycle and complies with a predetermined programme where different cleaning solutions, temperatures and circulation times are carefully tried out and specified. The cleaning is followed by a pre-sterilisation using hot water in the same circulation cycle.

In the developed world, extremely large units have recently been made operational for the production of foods. Ever increasing quantities of food are produced for a steadily growing market. As a result, the demands on available production time have also increased. Uninterrupted production times of up to 20 hours per day are at present not uncommon occurrences. In order to be able to increase the available production time further, it is necessary to shorten the time needed for cleaning the equipment without, to this end, any deterioration in the effectivity of the cleaning methods. Naturally, long production times also require that the cleaning operation be highly effective, since long production times give increased so-called fouling of the product on hot surfaces. For aseptic products and ESL products, a programme for cleaning and pre-sterilisation takes more than three hours to complete today.

OBJECTS OF THE INVENTION

One object of the present invention is to render more effective and shorten the time for cleaning and pre-sterilisation, without any reduction in the quality level of the cleaning per se.

SOLUTION

This and other objects have been attained according to the present invention in that the method of the type described by way of introduction has been given the characterising feature that a pre-sterilisation of the plant takes place simultaneously with the last circulation employing alkaline detergent solution.

Preferred embodiments of the present invention have further been given the characterising features as set forth in the appended subclaims.

BRIEF DESCRIPTION OF THE ACCOMPANYING DRAWINGS

Figure 2:
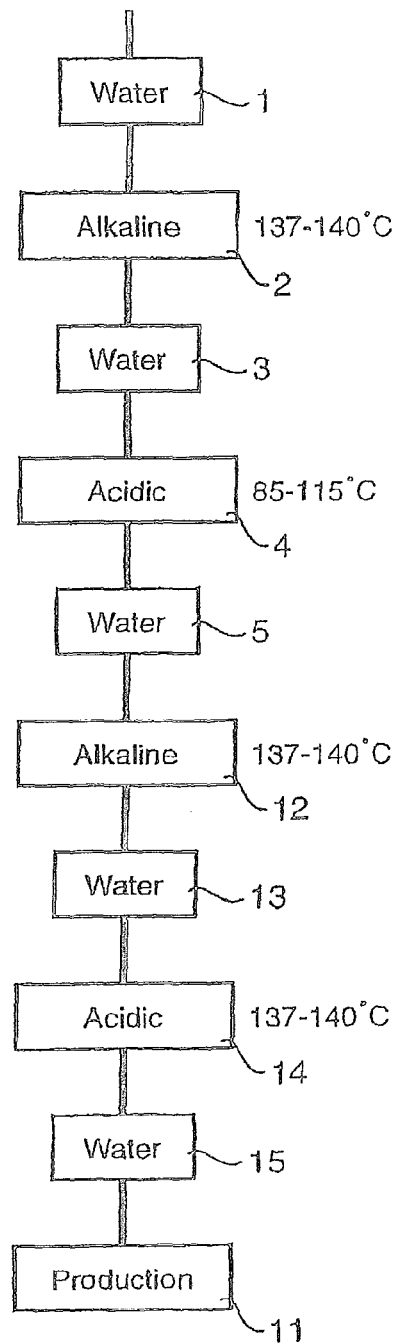

The present invention will now be described in greater detail hereinbelow, with reference to the accompanying Drawings. In the accompanying Drawings:

FIG. 1 is a diagram of a prior art cleaning method; and
FIG. 2 is a diagram of a cleaning method according to the present invention.

DESCRIPTION OF PREFERRED EMBODIMENT

The block diagram in FIG. 1 shows the major method steps for a cleaning programme which many large-scale dairies employ today. The programme is adapted for production times of up to 20 hours. The plant consists of a conventional plant for the production of an aseptic product or a product having extended shelf life, for example a UHT plant for the production of aseptic milk. The UHT plant consists of some form of heating equipment which may be direct or indirect. All heating of cleaning solution, as well as water for sterilising the plant takes place in this equipment. The plant also comprises tanks, conduits, valves, pumps, filling machines etc. The major proportion of this equipment is manufactured from stainless steel.

After the end of the product run, product residues are, as far as is possible, drained from the plant. The first step in the cleaning programme is a rinsing of the circulation cycle with water. Thereafter, a predetermined quantity of alkaline detergent solution is metered. The alkaline detergent solution consists substantially of caustic soda (NaOH) with various additives for en effective cleaning. The alkaline detergent solution is heated to 137 to 140° C. and is caused to circulate through the plant for 30 to 35 minutes, which constitutes method step 2. After the circulation of the alkaline detergent solution 2, a new rinsing with water 3 takes place.

The next step in the cleaning programme employs an acidic cleaning solution which is metered in a predetermined quantity. The acidic solution is heated to 85 to 115° C. and is caused to circulate through the plant for approximately 15 minutes. The acidic circulation constitutes method step 4. After the circulation of the acidic cleaning solution, a new rinsing with water 5 takes place.

The next method step in a conventional cleaning programme is a second circulation of alkaline detergent solution 6 which is heated to 85 to 115° C. and is caused to circulate for approximately 20 minutes. This second circulation of the alkaline detergent solution 6 is followed by rinsing with water 7. Thereafter, a second circulation with acidic cleaning solution 8 takes place at a temperature of 85 to 115° C. for roughly 10 minutes. Finally, a new rinsing with water 9 takes place and the cleaning programme proper is completed.

As is shown in FIG. 1, there then follows a pre-sterilisation 10 of the plant. The pre-sterilisation consists of heating of water to 137 to 140° C., circulation at this temperature during approximately 30 minutes and final cooling. The pre-sterilisation 10 takes roughly one hour to complete. The plant is now ready for production 11. A cleaning programme with subsequent pre-sterilisation, as shown in FIG. 1, takes a good three hours to complete.

FIG. 2 shows a method of cleaning a food plant according to the present invention. The plant is intended for the production of a sterile product, such as UHT milk, or a product with extended shelf life, such as a dairy product which is cold stored. The method is preferably intended for plants that operate on long production times.

A food plant for which the method according to the present invention is intended comprises heating equipment which may be of the direct type, and then consists of an injector, or alternatively an infusor. The heating may also be put into effect indirectly in a heat exchanger which may be of the plate heat exchanger type, or alternatively the tube heat exchanger type. All heating of detergent solutions takes place in the heating equipment. The plant also includes conduits, valves, pumps, tanks, filling machines etc. The greater proportion of the equipment of the plant is manufactured from stainless steel.

After a completed product run, product residues are drained as far as is possible from the plant and the cleaning programme thereafter begins with rinsing of the circulation cycle with water 1. Thereafter, a predetermined amount of alkaline detergent solution is metered. The alkaline detergent solution consists substantially of caustic soda (NaOH) with various additives in order to obtain as effective a cleaning solution as possible. The alkaline detergent solution is heated to 137 to 140° C. and is caused to circulate through the plant for 30 to 35 minutes, method step 2 according to FIG. 1. The circulation of the alkaline cleaning solution 2 is followed by a new rinsing with water 3.

The next step in the cleaning programme is a circulation of an acidic cleaning solution 4. The acidic cleaning solution is metered in a predetermined quantity and heated to 85 to 115° C., whereafter it is caused to circulate in the plant for approximately 15 minutes. After the circulation of the acidic cleaning solution 4, the plant is once again rinsed with water 5.

The next step in the method according to the present invention consists of a second circulation of the alkaline detergent solution 12, but where, after the input metering of the detergent solution, this is heated to 137 to 140° C. By causing the alkaline detergent solution to circulate for 30 minutes at this temperature, the plant is pre-sterilised at the same time as the plant is cleaned. This method step 12 entails that no additional pre-sterilisation of the plant is needed. By combining the cleaning programme with pre-sterilisation, the time during which the plant is inoperative can be reduced by approximately one hour. The circulation of the alkaline detergent solution 12 is followed by a rinsing with sterile water 13.

After the combined circulation of an alkaline detergent solution 12 and the sterilisation of the plant, the sterility in the plant must be maintained. This is put into effect in that all liquids that pass through the aseptic section of the plant must be sterile, i.e. all liquids must be heated to 137 to 140° C. for four seconds or a corresponding combination of temperature and time.

There then follows a rapid circulation or rather a through-flushing of an acidic cleaning solution 14 at a temperature of 137 to 140° C. The cleaning programme and the pre-sterilisation of the plant are completed by a rinsing with sterile water 15 and the plant is ready for production.

As will have been apparent from the foregoing description, the present invention realises a method for cleaning and pre-sterilisation of a food plant for the production of a sterile product or a product with extended shelf life. The method enjoys all of the advantages of prior art methods and realises an effective and reliable cleaning which combines the cleaning programme with the pre-sterilisation. By employing the method in a food plant, the time for cleaning and pre-sterilisation will be shortened, a time gain that can be utilised to increase the available production time.

What is claimed is:

1. A method of cleaning a food plant of the type which produces an aseptic product or a product with extended shelf life, the method comprising:
    circulating a heated first alkaline detergent solution through a circulation cycle of the food plant;
    circulating first rinsing water through the circulation cycle of the food plant following circulation of the heated first alkaline detergent solution through the circulation cycle of the food plant;
    circulating an acidic cleaning solution which is at a first temperature through the circulation cycle of the food plant following circulation of the first rinsing water through the circulation cycle of the food plant;
    circulating second rinsing water through the circulation cycle of the food plant following circulation of the acidic cleaning solution through the circulation cycle of the food plant; and
    circulating through the circulation cycle of the food plant a heated second alkaline detergent solution which is at a second temperature higher than the first temperature to effect pre-sterilization of the circulation cycle, the second alkaline detergent solution being circulated at a temperature of from 137° C. to 140° C., the circulation of the heated second alkaline detergent solution following the circulation of the second rinsing water.

2. The method as claimed in claim 1, wherein no pre-sterilization takes place after a last cleaning solution circulation.

3. The method as claimed in claim 1, wherein the circulation of the second alkaline detergent solution continues for approximately 30 minutes.

4. The method as claimed in claim 1, wherein following the circulation of the heated second alkaline detergent solution which is at the second temperature, no additional-pre-sterilization is performed.

5. The method as claimed in claim 2, wherein following the circulation of the heated second alkaline detergent solution which is at the second temperature, no additional-pre-sterilization is performed.

6. The method as claimed in claim 5, wherein the circulation of the second alkaline detergent solution continues for approximately 30 minutes.

7. The method of cleaning a food plant as claimed in claim 1, wherein in the plant, the first alkaline detergent solution is circulated at a temperature of from 137 to 140° C., the acidic cleaning solution is circulated at a temperature of from 85 to 115° C., the circulation of the second alkaline detergent solution is followed by a rapid circulation of a further acidic cleaning solution at a temperature of from 137 to 140° C., and further comprising circulating third sterile rinsing water through the circulation cycle of the food plant after the second alkaline detergent solution is circulated.

8. The method as claimed in claim 7, wherein no pre-sterilization takes place after a last cleaning solution circulation.

9. The method as claimed in claim 7, wherein the circulation of the second alkaline detergent solution continues for approximately 30 minutes.

* * * * *